United States Patent [19]

Crainich

[11] Patent Number: 5,464,300

[45] Date of Patent: Nov. 7, 1995

[54] MEDICAL INSTRUMENT AND COUPLING APPARATUS FOR SAME

[76] Inventor: Lawrence Crainich, Ceda Rd., Charlestown, N.H. 03603

[21] Appl. No.: 136,669

[22] Filed: Oct. 15, 1993

Related U.S. Application Data

[63] Continuation-in-part of Ser. No. 55,639, Apr. 29, 1993, Pat. No. 5,407,293.

[51] Int. Cl.$^6$ ...................................................... B25G 3/00
[52] U.S. Cl. ......................... 403/322; 403/325; 403/327; 403/348; 403/353; 403/354; 403/DIG. 4; 604/22
[58] Field of Search .............................. 403/348, DIG. 4, 403/322, 325, 327, 349, 350, 353, 354; 604/22, 167, 174

[56] References Cited

U.S. PATENT DOCUMENTS

| 4,986,690 | 1/1991 | Cooksey | 403/348 X |
| 5,088,853 | 2/1992 | Reid | 403/348 X |

Primary Examiner—David H. Corbin
Assistant Examiner—Christopher J. Novosad
Attorney, Agent, or Firm—Bachman & LaPointe

[57] ABSTRACT

A medical instrument includes a handle for manipulating the instrument, a tool head, and a tube element for joining the handle and the tool head, the tube element having a first end and a second end, a first coupling for releasably coupling the first end of the tube element and the handle, and a second coupling for releasably coupling the second end of the tube element and the tool head, whereby the tool head, tube element and handle are all readily separable from each other.

20 Claims, 4 Drawing Sheets

MEDICAL INSTRUMENT AND COUPLING APPARATUS FOR SAME

REFERENCE TO RELATED APPLICATIONS

The present application is a continuation-in-part of U.S. patent application Ser. No. 08/055,639, now U.S. Pat. No. 5,407,293, filed Apr. 29, 1993.

BACKGROUND OF THE INVENTION

The invention relates to a medical instrument, particularly to an instrument having a tool head and a handle joined by a tube, and to a coupling apparatus for coupling one or more of the aforesaid tool elements.

Conventional medical instruments typically include a tool head such as a surgical stapler, scissors, trocar, graspers or the like, connected to a handle through a tube element. The tube element is typically an elongated member which allows the tool head to be properly positioned for use in a patient as necessary. Such instruments are particularly useful in laparascopic procedures.

Obviously, with such a device sterilization of the instrument is a critical concern.

One approach to ensuring sterility in such an instrument is to provide the entire instrument as a single piece manufactured from plastic or the like so that the entire instrument can economically be discarded after use. This approach avoids the problem of sterilization. However, numerous tool elements and mechanisms, especially those contained in the handle, are unnecessarily discarded.

Another approach is to provide a handle and intermediate tube element as a single unit, for use with disposable tool units or tool cartridges. With this approach, the tool head or unit is discarded after use while the handle and tube are sterilized for reuse. With this approach, however, the tube can become sufficiently contaminated, because of its intimate contact with a patient during use, that the tube and handle structure must nevertheless be discarded. Further, the tube and handle structure can be an unwieldy and/or cumbersome structure to attempt to sterilize and may, therefore, not be sterilizable in conventional equipment such as conventional autoclaves.

It would be desirable to provide an instrument wherein the tube element, tool head and handle element are all conveniently separable elements of the instrument. Further, simple and reliable means are desirable for coupling such elements together, in either rotatable or non-rotatable manner.

It is therefore the primary object of the invention to provide a medical instrument wherein a tool head is joined to a handle element via a separate intermediate tube element which is conveniently separable from both the tool head and the handle.

It is a further object of the invention to provide a coupling apparatus for coupling the tool head, tube element and handle together in a secure, reliable, and conveniently separable manner.

It is a still further object of the invention to provide such a coupling apparatus wherein the coupled tool elements are coupled rotatably relative to each other.

It is another object to provide such a coupling apparatus wherein uncoupling of the apparatus is accomplished through a simple but deliberate procedure so that separation can be readily accomplished when desired, without risk of inadvertent separation.

Other objects and advantages will appear hereinbelow.

SUMMARY OF THE INVENTION

The foregoing objects and advantages are readily obtained by the present invention.

According to the invention, a medical instrument is provided wherein the elements of the instrument are coupled in a reliable but conveniently releasable manner so that individual elements can be sterilized or disposed of, as required.

The medical instrument includes, in accordance with the invention, a handle means for manipulating the instrument, a tool head, a tube element for joining the handle means and the tool head, the tube element having a first end and a second end, first coupling means for releasably coupling the first end of the tube element and the handle means, and second coupling means for releasably coupling the second end of the tube element and the tool head, whereby the tool head, tube element and handle means are all readily separable from each other.

Further according to the invention, the coupling means for coupling the handle and tube preferably provides rotatable coupling, and may comprise an insertion member, a receiving member sized to receive the insertion member, engaging means disposed on the insertion member and the receiving member for rotatably coupling the insertion member with the receiving member, the engaging means being rotatable between an engaged position wherein the insertion member and the receiving member are engaged against longitudinal separation, and a disengaged position wherein the receiving member and the insertion member can be longitudinally separated, and locking means for rotatably locking the engaging means, the locking means being positionable between a locked position wherein the engaging means is engaged throughout an entire rotation of the insertion member relative to the receiving member, and an unlocked position wherein the insertion member can be rotated relative to the receiving member to the disengaged position.

BRIEF DESCRIPTION OF THE DRAWINGS

A detailed description of the invention follows, with reference to the accompanying drawings, wherein.

DETAILED DESCRIPTION

The invention relates to a medical instrument wherein a tool head is mounted to a handle member through an elongated tube member which allows the tool head to be inserted or positioned within a patient during a medical procedure. Such an instrument is especially useful during laparascopic procedures.

According to the invention, the tool head, tube member and handle member are separate elements, joined or coupled together for use with coupling structures which advantageously allow the elements to be conveniently separated for individual disposal or sterilization and reuse as appropriate.

Figures 1, 2A:
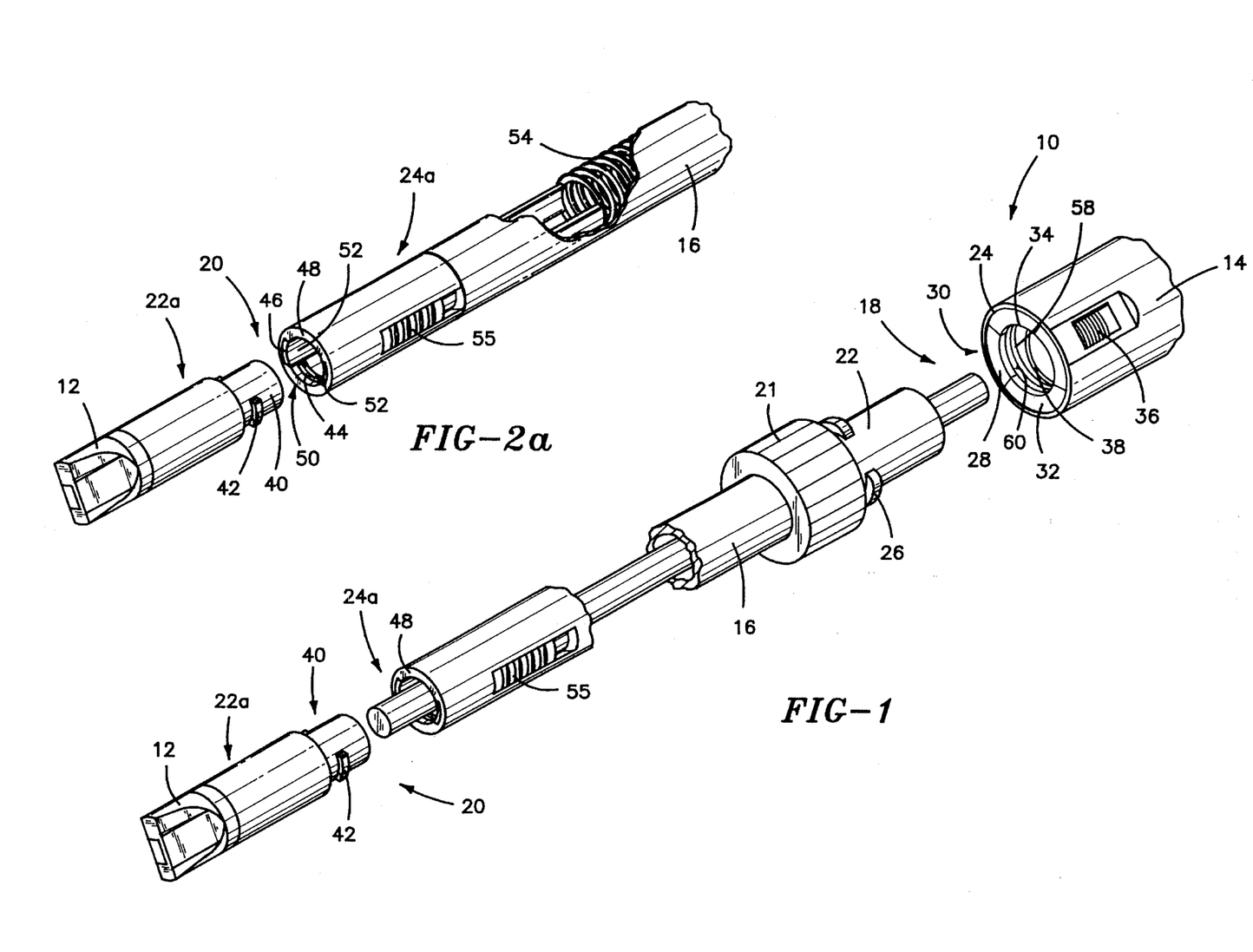
FIG. 1 illustrates a partially exploded view of a medical instrument according to the invention.
FIG. 2a is an exploded view of a coupling apparatus for non-rotatable coupling, according to the invention.

FIG. 1 shows an instrument 10, including a tool head 12, handle member 14, tube element 16 (partially broken away), a first coupling mechanism 18, for coupling tube element 16 and handle member 14, and a second coupling mechanism 20 for coupling tube element 16 and tool head 12.

According to the invention, coupling mechanisms 18, 20 provide secure and reliable but readily releasable coupling of the elements of the instrument 10. In this regard, the coupling mechanism may provide rotatable or non-rotatable coupling of the elements of the medical instrument, as desired. Typically, it is desirable to mount tool head 12 to tube member 16 in a non-rotatable manner. In some instances, however, it is desirable to have one element be rotatable relative to another. Such is the case for example with a surgical stapler, where it is desirable to provide rotation of the tool head 12 relative to handle 14 so that staples can be properly oriented for use. Thus, FIG. 1 shows a coupling mechanism 18 which, according to the invention, allows rotation of tube element 16 relative to handle 14 when tube 16 and handle 14 are coupled. FIG. 1 also shows the non-rotatable coupling, at coupling mechanism 20, of tool head 12 relative to tube 16. In this manner, advantageously, tool head 12 can be properly positioned for use by rotating tube 16 relative to handle 14. Proper positioning is obtained, for example, by rotating tube 16 via a tube gripping portion 21.

Figure 2:
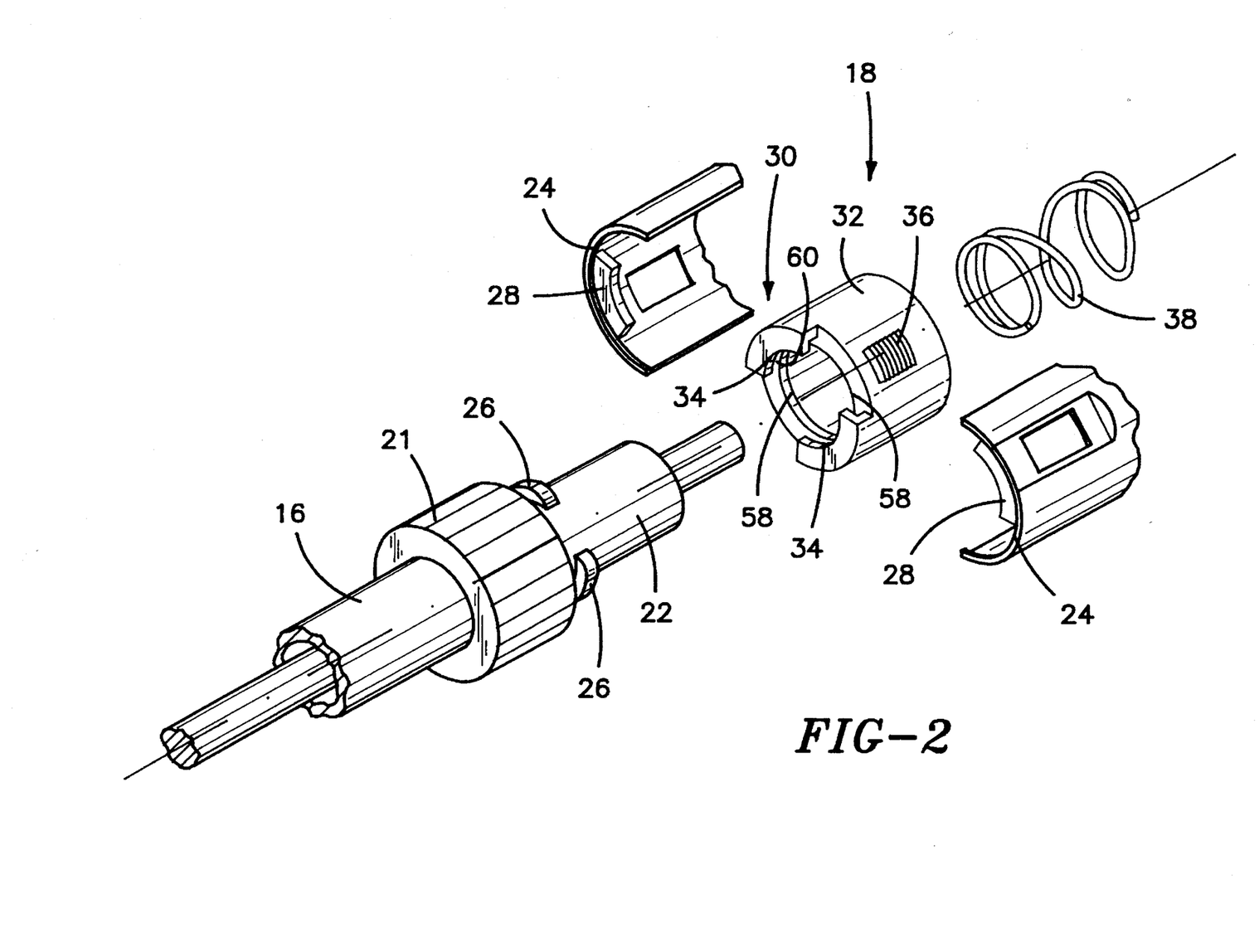
FIG. 2 is an exploded view of a coupling apparatus for rotatable coupling, according to the invention.

FIGS. 2 and 2a illustrate, respectively, preferred embodiments of a rotatable coupling 18 and a non-rotatable coupling 20. It should be understood that, as used herein, a rotatable coupling is a coupling device which allows rotation of one coupled element relative to the other coupled element in the coupled position after coupling; and a non-rotatable coupling is a coupling device which does not allow rotation of one coupled element relative to the other coupled element in the coupled position after coupling.

FIG. 2 shows a rotatable coupling 18 including an insertion member 22 attached to tube 16, and a receiving member 24 attached to handle 14 (not shown in FIG. 2). Insertion member 22 preferably comprises an elongate generally round or cylindrical member, and receiving member 24 is preferably a generally hollow member having an inside diameter sized to snugly receive insertion member 22. This fit is preferably provided with as narrow a tolerance as practical so as to avoid any wobble between tool elements. Outwardly projecting sections or ridges 26 are preferably defined on insertion member 22 and inwardly projecting sections or ridges 28 are also preferably defined within receiving member 24. Ridges 26 are preferably spaced on insertion member 22 so as to form gaps therebetween sufficient in size to accommodate ridges 28 of receiving member 24, and vice versa. In this manner, insertion member 22 and receiving member 24 can be engaged against longitudinal separation by aligning ridges 26 of insertion member 22 with the gaps formed between ridges 28 of receiving member 24, fully inserting insertion member 22 into receiving member 24, and rotating insertion member 22 relative to receiving member 24 so that ridges 26 at least partially align with and engage ridges 28 to prevent longitudinal separation of insertion member 22 and receiving member 24.

Receiving member 24 preferably includes a locking element 30 for rotatably locking insertion member 22 into place after it has been fully inserted into receiving member 24 and ridges 26, 28 are engaged. Locking element 30 preferably comprises a tubular hollow member or sleeve 32 slidably disposed within receiving member 24. Sleeve 32 preferably includes inwardly projecting ridges 34, and one or more gripping portions 36. Ridges 34 are sized and arranged on sleeve 32 so as to coincide with the gaps between ridges 28 of receiving member 24 when sleeve 32 is in a locking or locked position. Sleeve 32 is preferably slidable between a locked position wherein ridges 34 of sleeve 32 and ridges 28 of receiving member 24 define a substantially continuous ridge or series of ridges which are at least partially aligned with ridge 26 of insertion member 22, and thereby engaged with ridge 26, through an entire rotation of insertion member 22 relative to receiving member 24. Insertion member 22 and receiving member 24 are thereby rotatably locked when locking element 30 is in the locked position. A spring 38 or other biasing member is preferably disposed within receiving member 24 so as to bias sleeve 32 toward the locking position. Sleeve 32 is slidable, against spring 38, to an unlocked position wherein ridges 34 of sleeve 32 do not engage ridge 26 so that rotation of insertion member 22 to align ridges 26 with the gaps between ridges 28 allows insertion member 22 to be longitudinally withdrawn from receiving member 24.

When in the locked position, ridges 34 of sleeve 32 eliminate or reduce the size of gaps between ridges 28 of receiving member 24 so that rotation of insertion member 22 relative to receiving member 24 cannot align ridges 26 of insertion member 22 with a gap sufficient in size to allow longitudinal separation of insertion member 22 and receiving member 24. Such rotation without separation, however, is freely allowed when sleeve 32 is in the locked position, thereby allowing rotation of tube 16 and attached tool head 12 for proper positioning during use.

FIGS. 3–6 further illustrate the features of coupling mechanism 18 for providing rotatable connection.

Figure 3:
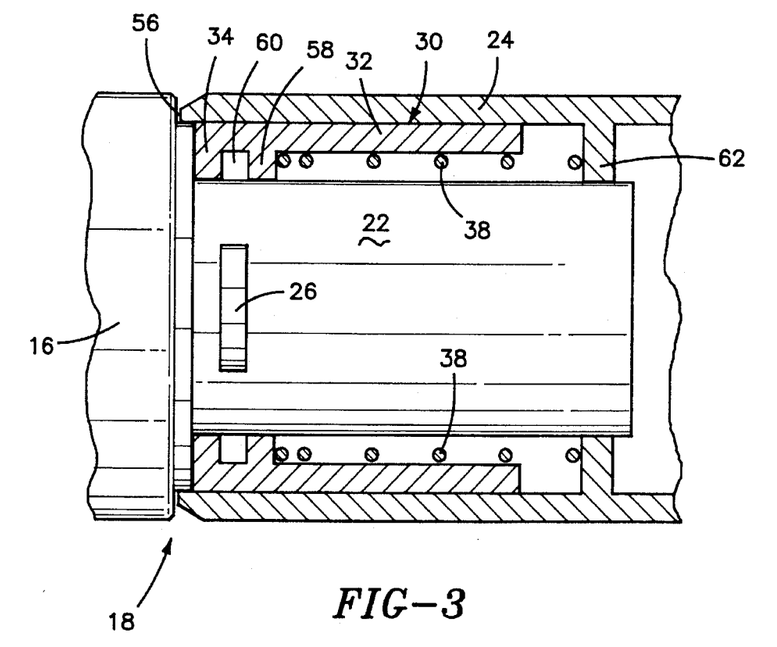
FIG. 3 is a cross-section of a coupling apparatus according to the invention, with an insertion member locked in an engaged position.

FIG. 3 shows an insertion member 22 rotatably locked within receiving member 24. Sleeve 32 is slidably disposed within receiving member 24, and is biased toward an open end 56 of receiving member 24 by spring 38.

As shown, sleeve 32 may preferably have an inner ridge 58 which, in conjunction with ridge 34, serves to define a groove 60 in which ridge 26 of insertion member 22 rotates when sleeve 32 is in the locked position.

Receiving member 24 also preferably has an additional inner ridge or lip 62. Lip 62 may serve as a diameter guide to prevent insertion member 22 from wobbling in receiving member 24. Lip 62 also serves as a seat for one end of spring 38, with the other end of spring 38 being disposed against inner ridge 58.

Figure 4:
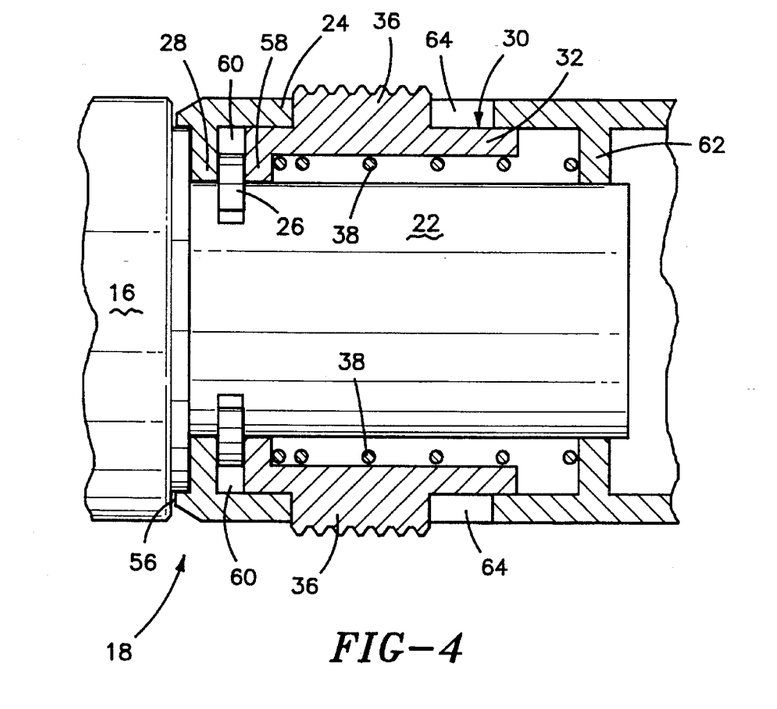
FIG. 4 is a cross-section similar to that of FIG. 3, but taken through a section perpendicular to that of FIG. 3.

FIG. 4 illustrates coupling mechanism 18 from a section taken perpendicular to that of FIG. 3. As shown, receiving member 24 preferably includes slots or cutouts 64 defined therein, and sleeve 32 has a like number of gripping members 36 which extend outwardly through slots 64 for use in manipulating sleeve 32 against the bias of spring 38 to the unlocked position. FIG. 4 also illustrates the portion of ridge 28 of receiving member 24 which cooperates with inner ridge 58 of sleeve 32 to further define groove 60.

FIGS. 3 and 4 show insertion member 22 with ridge 26 rotated to a position where it engages ridge 28 of receiving member 24 (see especially FIG. 4). Thus, insertion member 22 and receiving member 24 are engaged against longitudinal separation. Furthermore, rotation of insertion member 22 will not free insertion member 22 from receiving member 24 because ridges 34 of sleeve 32 block or fill the gaps between ridges 28 when sleeve 32 is in the locked position.

Figure 5:
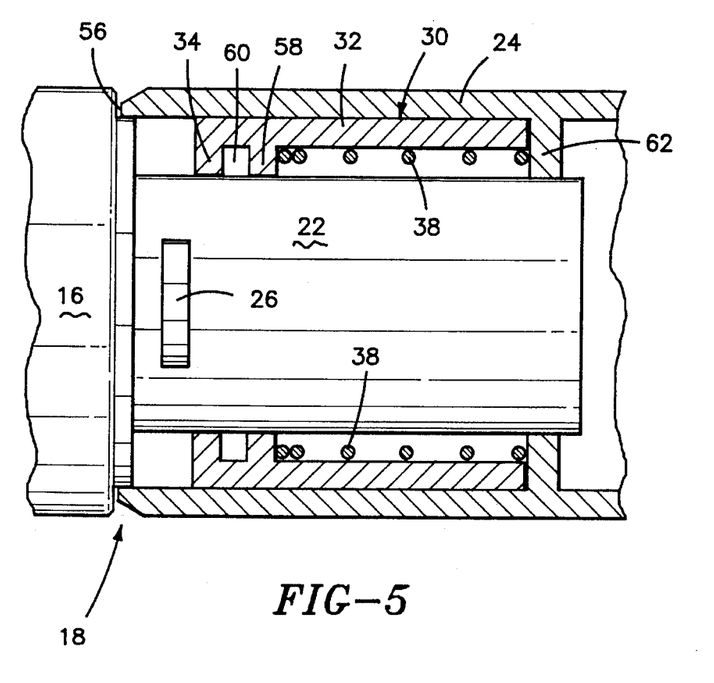
FIG. 5 is a cross-section similar to that of FIG. 3, with the locking sleeve withdrawn to an unlocked position.
Figure 6:
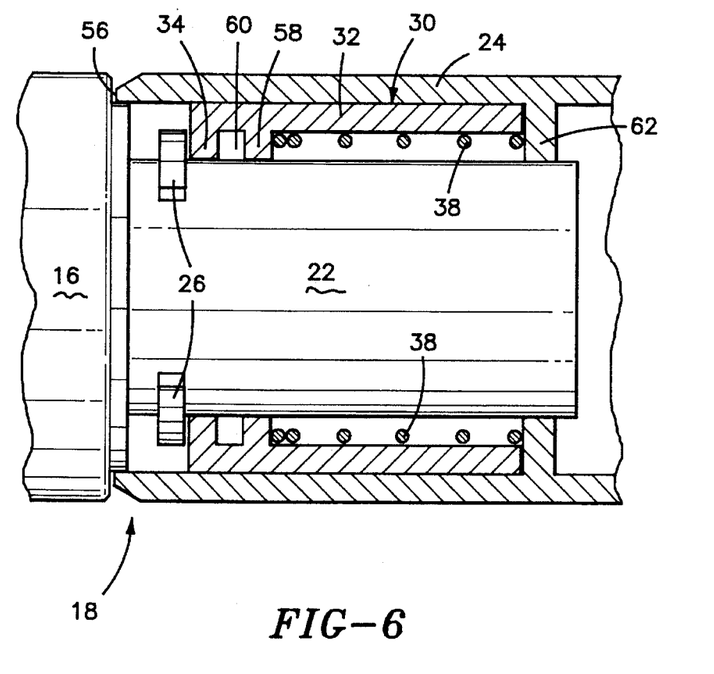
FIG. 6 is a cross-section similar to that of FIGS. 3 and 5, with the locking sleeve withdrawn and the insertion member rotated to a disengaged position for longitudinal separation.

FIG. 5 shows sleeve 32 withdrawn against the bias of spring 38 to the unlocked position. Note that ridges 34 of sleeve 32 no longer are in position to engage ridge 26 of insertion member 22. Thus, and as shown in FIG. 6, rotation of insertion member 22 relative to receiving member 24 when sleeve 32 is in the withdrawn or unlocked position aligns ridges 26 of insertion member 22 with the gaps between ridges 28 of receiving member 24, thereby allowing longitudinal separation of insertion member 22 and receiving member 24.

FIG. 2a shows a coupling mechanism 20 for non-rotatable coupling, here of tool head 12 and tube 16. In this embodiment, tool head 12 and tube 16 preferably have substantially the same outside diameter as shown for example in FIGS. 1 and 2a.

Tool head 12 is connected to tube 16, according to the invention, through a coupling apparatus which includes an insertion member 22a and a receiving member 24a. The tool head 12 shown in FIG. 2a is a disposable cartridge for surgical staples. As set forth above, however, the coupling apparatus of the present invention is useful for the attachment of any desired tool head to a tube or handle member.

Insertion member 22a preferably has a rearwardly protruding portion 40 which is sized to be received within receiving member 24a. According to the invention insertion member 22a and receiving member 24a are releasably coupled through an engaging or ridge and groove structure which firmly and releasably couples the two elements.

As shown, protruding portion 40 preferably has a substantially cylindrical outer surface and has at least one projection or ridge 42 disposed around a portion of the outer surface.

Receiving member 24a preferably has a substantially cylindrical inner surface, as shown, and is preferably sized so as to snugly receive protruding portion 40. This fit is preferably provided with as narrow a tolerance as practical so as to avoid any wobble between tool head 12 and tube 16.

Receiving member 24a preferably has at least one groove 44 defined around a portion of the inner surface thereof. Receiving member 24a also preferably has at least one longitudinal cutout or track 46 defined longitudinally along the inner surface thereof to receive ridge 42 of protruding portion 40. Receiving member 24a has an edge 48 facing insertion member 22a, and longitudinal track 46 extends to edge 48, so that track 46 can receive ridge 42. Longitudinal track 46 is preferably sized so as to accommodate ridge 42 of protruding portion 40. Thus, longitudinal track 46 preferably extends at least as far radially and circumferentially around the inner surface of receiving member 24a as does ridge 42 of protruding portion 40. Preferably, longitudinal tracks 46 are provided in a like number to the number of ridges 42 on protruding portion 40, and are also provided in similar circumferential spacing as ridges 42.

In this manner, ridges 42 can be aligned with tracks 46 at edge 48 so as to allow protruding portion 40 to be readily and freely inserted into receiving member 24a.

Longitudinal tracks 46 intersect groove 44. In this manner, insertion member 22a can then be rotated relative to receiving member 24a so as to rotate ridges 42 into groove 44, thereby engaging insertion member 22a with receiving member 24a, and radially orienting tool head 12.

Further according to the invention, at least one locking member 50 is preferably disposed in at least one track 46. Locking member 50 is preferably slidably disposed in receiving member 24a and is slidable between an extended position, as shown in FIG. 2a, and a withdrawn position (not shown).

Locking member 50 may preferably have an arm 52 disposed in each track 46, and may be biased by any known and convenient means, such as spring 54, toward the extended position.

When locking member 50 is in the extended position, arms 52 occupy tracks 46 at the point of intersection of track 46 and groove 44. That is, arms 52 extend into a plane of rotation of insertion member 22a relative to receiving member 24a. Thus, when locking member 50 is in the extended position, with insertion member 22a inserted into receiving member 24a with ridges 42 rotated into groove 44, ridges 42 are retained in groove 44 and cannot be rotated out of groove 44 into track 46. Thus, when locking member 50 is in the extended position, the apparatus according to the invention is locked against rotation out of the engaged position, and is radially oriented.

Locking member 50 also preferably has a gripping portion 55 which is accessible from outside of the receiving member 24a so as to allow locking member 50 to be manipulated longitudinally between the extended position and the withdrawn position.

Arms 52 and ridges 42 may preferably be sized so that arms 52 abut both sides of ridge 42 when the apparatus is locked together so as to prevent rotation of tool head 12 relative to tube 16 and to maintain correct radial orientation thereof.

It is noted that either coupling mechanism 18, 20 could suitably be used to connect a tool head 12 directly to handle 14 in situations where no tube 16 is necessary. In this situation, insertion member 22, 22a and receiving member 24, 24a, in accordance with the invention, would be connected directly between tool head 12 and handle 14.

It is also noted that, while the drawings attached hereto generally depict tool head 12 as a surgical stapler cartridge, any other suitable and desired medical instrument could be utilized in accordance with the invention.

It should further be noted that, while the description of the above embodiments has receiving member 24, 24a and insertion member 22, 22a attached to specific elements of tool head 12, handle 14, and tube 16, receiving member 24 and insertion member 22 could of course be switched, or positioned in an opposite configuration, for example with receiving member 24 on tube 16 and insertion member 22 on handle 14, all in keeping with the present invention.

Finally, it should also be noted that ridges 26, 28, while shown in pairs, may of course be utilized in any other number provided that sufficient gaps between one set of ridges are left to accommodate the other set of ridges. Further, several ridges could be provided on one member and just a single or different number of ridges provided on the other.

The present invention allows the manufacture of a medical instrument in components, namely tool head 12, handle 14 and tube 16, which are readily separable for disposal or sterilization as appropriate. If both handle 14 and tube 16 are to be sterilized, separation of the two allows sterilization in a broader range of autoclave type equipment by rendering the elements of instrument 10 less bulky and cumbersome, and thereby more manageable.

Further, if the application of instrument 10 is such that tube 16 is irretrievably contaminated and cannot safely be sterilized and reused, tube 16 can be discarded without abandoning handle 14, which may contain complicated, intricate and/or expensive mechanical features which are preferably not wasted. Thus, in accordance with the invention, at least handle 14 is saved and reusable after use.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A medical instrument, comprising:

handle means for manipulating the instrument;

a tool head;

a tube element for joining the handle means and the tool head, the tube element having a first end and a second end;

first coupling means for releasably coupling the first end of the tube element and the handle means in a coupled position wherein the tube element is rotatable relative to the handle means after could, and wherein the first coupling means comprises:

an insertion member;

a receiving member sized to receive the insertion member, each of the tube element and handle means being connected to one of the insertion member and the receiving member;

engaging means disposed on the insertion member and the receiving member for rotatably coupling the insertion member with the receiving member, the engaging means being rotatable between an engaged position wherein the insertion member and the receiving member engaged against longitudinal separation, and a disengaged position wherein the receiving member and the insertion member can be longitudinally separated;

locking means for rotatably locking the engaging means, the locking means being positionable between a locked position wherein the engaging means is engaged throughout an entire rotation of the insertion member relative to the receiving member, and an unlocked position wherein the insertion member can be rotated relative to the receiving member to the disengaged position; and second coupling means for releasably coupling the second end of the tube element and the tool head in a coupled position wherein the tool head is not rotatable relative to the tube element after coupling, whereby the tool head, tube element and handle means are all readily separable from each other.

2. An apparatus according to claim 1, wherein the engaging means includes at least one radially inwardly projecting section and at least one radially outwardly projecting section, one of the radially inwardly and outwardly projecting sections being disposed on the insertion member and one of the radially inwardly and outwardly projecting sections being disposed on the receiving member, the insertion member and the receiving member being rotatable relative to one another between an engaged position wherein the radially inwardly projecting section and the radially outwardly projecting section are at least partially aligned so as to prevent longitudinal separation of the insertion member and the receiving member, and a disengaged position wherein the radially inwardly projecting section and the radially outwardly projecting section are not aligned so as to allow longitudinal separation of the insertion member and the receiving member.

3. An apparatus according to claim 2, wherein the locking means, when in the locked position, defines additional sections of at least one of the inwardly projecting section and the outwardly projecting section so that the inwardly projecting sections and the outwardly projecting sections are at east partially aligned and engaged at substantially all rotational positions of the insertion member relative to the receiving member.

4. An apparatus according to claim 2 wherein the insertion member is a generally cylindrical structure and the outwardly projecting section is a radial ridge disposed around a portion of the insertion member, and wherein the receiving member is a generally hollow structure sized for receiving the insertion member therein, and the inwardly projecting section is a radial ridge disposed around a portion of an inner surface of the receiving member.

5. An apparatus according to claim 4, wherein the insertion member has at least two outwardly projecting sections defining gaps therebetween, and wherein the receiving member has at least two inwardly projecting sections defining gaps therebetween, and wherein the gaps of the insertion member and receiving member are sufficient in size to allow passage of respective inwardly and outwardly projecting sections when the insertion member and the receiving member are in the disengaged position.

6. An apparatus according to claim 5, wherein the locking means is slidably disposed on the receiving member and has additional inwardly projecting sections, the locking means being longitudinally slidable relative to the receiving member between a locked position wherein the additional inwardly projecting sections substantially fill the gaps of the receiving member and an unlocked position wherein the additional inwardly projecting sections are longitudinally withdrawn from the gaps of the receiving member.

7. An apparatus according to claim 6, wherein the locking means comprises a hollow sleeve disposed longitudinally slidable relative to the receiving member between the locked position and the unlocked position, and wherein the additional inwardly projecting sections are arranged around an inner surface of the hollow sleeve.

8. An apparatus according to claim 7, wherein the receiving member includes at least one cutout passing therethrough and the hollow sleeve is slidably positioned within the receiving member and has at least one gripping member extending through the cutout whereby the hollow sleeve can be longitudinally displaced between the locked position and the unlocked position.

9. An apparatus according to claim 8, further including biasing means for biasing the hollow sleeve toward the locked position.

10. An apparatus according to claim 1, wherein the tool head and the tube element have substantially the same outside diameter.

11. A coupling apparatus for rotatably coupling two elements of a medical device, the coupling apparatus comprising:

an insertion member;

a receiving member sized to receive the insertion member;

engaging means disposed on the insertion member and the receiving member for rotatably coupling the insertion member with the receiving member, the engaging means being rotatable between an engaged position wherein the insertion member and the receiving member are engaged against longitudinal separation, and a disengaged position wherein the receiving member and the insertion member can be longitudinally separated; and locking means for rotatably locking the engaging means, the locking means being positionable between a locked position wherein the engaging means is engaged throughout an entire rotation of the insertion member relative to the receiving member, and an unlocked position wherein the insertion member can be rotated relative to the receiving member to the disengaged position.

12. An apparatus according to claim 11, wherein the engaging means includes at least one radially inwardly projecting section and at least one radially outwardly projecting section, one of the radially inwardly and outwardly projecting sections being disposed on the insertion member and one of the inwardly and outwardly projecting sections being disposed on the receiving member, the insertion member and the receiving member being rotatable relative to one another between an engaged position wherein the inwardly projecting section and the outwardly projecting section are at least partially aligned so as to prevent longitudinal separation of the insertion member and the receiving member, and a disengaged position wherein the inwardly projecting section and the outwardly projecting section are not aligned so as to allow longitudinal separation of the insertion member and the receiving member.

13. An apparatus according to claim 12, wherein the locking means, when in the locked position, defines additional sections of at least one of the inwardly projecting section and the outwardly projecting section so that the inwardly projecting sections and the outwardly projecting sections are at east partially aligned and engaged at substantially all rotational positions of the insertion member relative to the receiving member.

14. An apparatus according to claim 12, wherein the insertion member is a cylindrical structure and the outwardly projecting section is a radial ridge disposed around a portion of the insertion member, and wherein the receiving member is a hollow structure sized for receiving the insertion member therein, and the inwardly projecting section is a radial ridge disposed around a portion of an inner surface of the receiving member.

15. An apparatus according to claim 14, wherein the insertion member has at least two outwardly projecting sections defining gaps therebetween, and wherein the receiving member has at least two inwardly projecting sections defining gaps therebetween, and wherein the gaps of the insertion member and receiving member are sufficient in size to allow passage of respective inwardly and outwardly projecting sections when the insertion member and the receiving member are in the disengaged position.

16. An apparatus according to claim 15, wherein the locking means is disposed in a longitudinally slidable manner relative to the receiving member and has additional inwardly projecting sections, the locking means being longitudinally slidable relative to the receiving member between a locked position wherein the additional inwardly projecting sections substantially fill the gaps of the receiving member and an unlocked position wherein the additional inwardly projecting sections are longitudinally withdrawn from the gaps of the receiving member.

17. An apparatus according to claim 16, wherein the locking means comprises a hollow sleeve disposed on the receiving member and longitudinally slidable thereon between the locked position and the unlocked position, and wherein the additional inwardly projecting sections are arranged around an inner surface of the hollow sleeve.

18. An apparatus according to claim 17, wherein the receiving member includes at least one cutout passing therethrough and the hollow sleeve is slidably positioned within the receiving member and has at least one gripping member extending through the cutout whereby the hollow sleeve can be longitudinally displaced between the locked position and the unlocked position.

19. An apparatus according to claim 18, further including biasing means for biasing the hollow sleeve toward the locked position.

20. A medical instrument, comprising:

handle means for manipulating the instrument;

a tool head;

a tube element for joining the handle means and the tool head, the tube element having a first end and a second end;

first coupling means for releasably coupling the first end of the tube element and the handle means in a coupled position wherein the tube element is rotatable and longitudinally fixed during rotation relative to the handle means after coupling, and second coupling means for releasably coupling the second end of the tube element and the tool head in a coupled position wherein the tool head is not rotatable relative to the tube element after coupling, whereby the tool head, tube element and handle means are all readily separable from each other.

* * * * *

UNITED STATES PATENT AND TRADEMARK OFFICE
CERTIFICATE OF CORRECTION

PATENT NO. : 5,464,300
DATED : November 7, 1995
INVENTOR(S) : LAWRENCE CRAINICH

It is certified that error appears in the above-indentified patent and that said Letters Patent is hereby corrected as shown below:

In Column 7, claim 1, line 26, "could" should read --coupling--;

In Column 7, claim 1, line 38, before "engaged" --are-- should be inserted;

In Column 8, claim 3, line 11, "east" should read --least--; and

In Column 9, claim 13, line 36, "east" should read --least--.

Signed and Sealed this

Fifth Day of March, 1996

Attest:

BRUCE LEHMAN

Attesting Officer

Commissioner of Patents and Trademarks